United States Patent [19]

Anderson

[11] Plant 4,081

[45] July 19, 1977

[54] NECTARINE TREE

[75] Inventor: Frederic W. Anderson, Merced, Calif.

[73] Assignee: Reedley Nursery, Inc., Reedley, Calif.

[21] Appl. No.: 721,542

[22] Filed: Sept. 8, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is of medium size, medium vigor, spreading, foliated with large, acutely pointed, lanceolate leaves which are smooth and have a crenate margin, a regular and productive bearer of large to medium size, uniform, symmetrical, globose, freestone fruit having yellow skin substantially overspread with red, yellow flesh, and a red pit cavity with the red streaked into the flesh, and the stone having a sweet kernel.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard located as aforesaid, as an $F_1$ cross between the May Grand nectarine (U.S. Plant Pat. No. 2,794) as the pollen parent, and the Red Free nectarine (U.S. Plant Pat. No. 3,228) as the seed parent. The variety, as thus originated, and under careful and continuing observation, evidenced — upon bearing fruit — certain novel characteristics which were commercially desirable, and I, therefore, undertook asexual reproduction of the variety preparatory to introducing it to the trade.

ASEXUAL REPRODUCTION OF THE VARIETY

Subsequent to origination and selection by me of the present variety of nectarine tree, in the manner above described, I asexually reproduced it by top-working on mature trees in my said experimental orchard, and — in maturity — such reproductions ran true to the original tree in all respects.

SUMMARY OF THE VARIETY

The present variety of nectarine tree is of medium size, medium vigor, spreading, foliated with large, acutely pointed, lanceolate leaves which are smooth and have a crenate margin, a regular and productive bearer of large to medium size, uniform, symmetrical, globose, freestone fruit having yellow skin substantially overspread with red, yellow flesh, and a red pit cavity with the red streaked into the flesh, and the stone having a sweet kernel; the variety being particularly characterized by fruit which resembles the pollen parent, May Grand, in its attractive red skin and juicy flesh, and resembles the seed parent, Red Free, in most other respects, but ripens about one week later than said Red Free.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

DESCRIPTION OF THE VARIETY

The botanical details of this new and distinct variety of nectarine tree — with color definitions (except those in common color terms) referencd to Maerz and Paul Dictionary of Color — are as follows:

Tree:
- *Size.*—Medium.
- *Vigor.*—Medium.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Large; average length — 6½"; average width — 1¾".
- *Form.*—Lanceolate; acutely pointed.
- *Thickness.*—Medium.
- *Texture.*—Smooth.
- *Margin.*—Crenate.
- *Petiole.*—Medium to short — average — ½'; Medium thickness.
- *Glands.*—Average number and position — 2 on petiole and 2 on blade; alternate; medium size; reniform.
- *Color.*—Top side — Medium green (23-L-7); under side — Lighter green (22-K-6).

Flower buds:
- *Size.*—Medium.
- *Length.*—Medium.
- *Form.*—Plump.

Flowers:

*Blooming period.*—Medium, as compared with other varieties.

*Size.*—Large.

Fruit:

*Maturity when described.*—Eating ripe.

*Date of first picking.*—Aug. 14th, 1976.

*Date of last picking.*—Aug. 22nd, 1976.

*Size.*—Large to medium; variable; average diameter axially — $2\frac{3}{8}''$; average transversely in suture plane — $2\frac{3}{8}''$.

*Form.*—Uniform; symmetrical; globose.

*Suture.*—Shallow; extends from base to apex, with slight depression beyond pistil point.

*Ventral surface.*—Rounded strongly.

*Cavity.*—Rounded, with suture showing on both sides.

*Base.*—Rounded.

*Apex.*—Short; depressed.

*Pistil point.*—Inconspicuous.

Skin:

*Thickness.*—Medium.

*Texture.*—Medium.

*Tenacity.*—Parts easily from flesh.

*Tendency to crack.*—Slight.

*Down.*—Wanting.

*Color.*—Yellow (9-L-5) substantially overspread with red (5-L-5) shading to darker red (7-L-6), with some yellow speckling and red mottling.

Flesh:

*Amygdalin.*—Wanting.

*Juice.*—Moderate; rich.

*Texture.*—Firm to medium; fine; crisp; meaty to melting.

*Fibers.*—Fine.

*Ripens.*—Evenly.

*Flavor.*—Subacid; mild; delicate.

*Aroma.*—Wanting.

*Eating quality.*—Good.

*Color.*—Yellow (10-L-5).

*Surface of pit cavity.*—Red (5-L-5), with white fibers; the red streaking into the flesh.

Stone:

*Type.*—Free.

*Size.*—Medium; average length — $1\frac{1}{4}''$; average breadth — $1\frac{1}{8}''$; average thickness — $\frac{7}{8}''$.

*Form.*—Oblong.

*Base.*—Straight.

*Hilum.*—Narrow.

*Apex.*—Acute.

*Sides.*—Equal.

*Ridges.*—Rounded.

*Pits.*—Angular.

*Ventral edge.*—Thin.

*Dorsal edge.*—Full, with narrow groove throughout.

*Tendency to split.*—Slight.

*Kernel.*—Sweet.

*Color.*—Red (7-J-6).

Use: Market — local; dessert; culinary; canning.

Keeping quality: Medium.

Resistance to insects and diseases: No unusual susceptibilities noted.

Shipping quality: Medium.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is of medium size, medium vigor, spreading, foliated with large, acutely pointed, lanceolate leaves which are smooth and have a crenate margin, a regular and productive bearer of large to medium size, uniform, symmetrical, globose, freestone fruit having yellow skin substantially overspread with red, yellow flesh, and a red pit cavity with the red streaked into the flesh, and the stone having a sweet kernel; the variety being particularly characterized by fruit which resembles the pollen parent, May Grand, in its attractive red skin and juicy flesh, and resembles the seed parent, Red Free, in most other respects, but ripens about one week later than said Red Free.

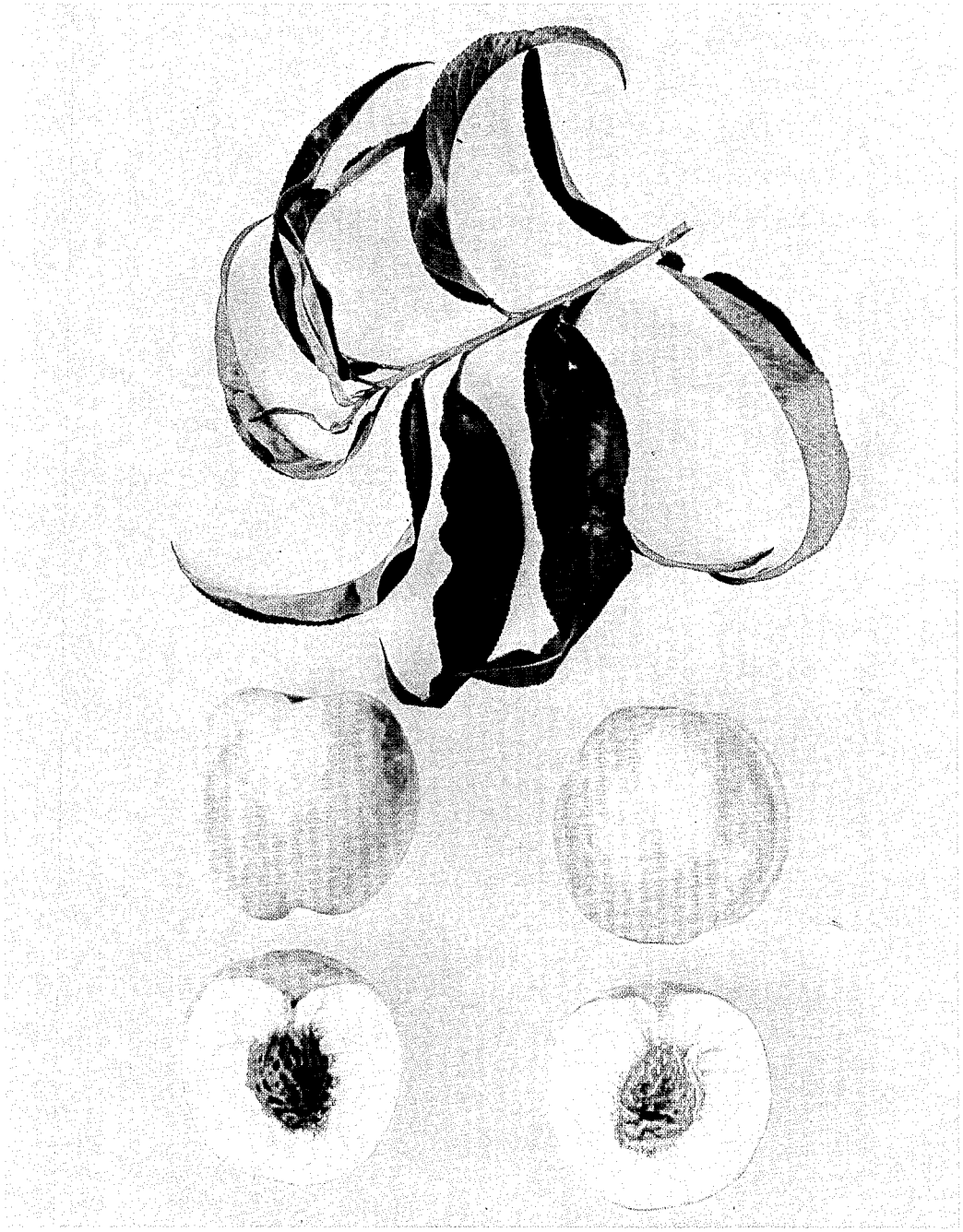

* * * * *